(12) United States Patent
Talanian (10) Patent No.: US 8,725,421 B2
(45) Date of Patent: May 13, 2014

(54) IN VITRO ESTIMATION OF IN VIVO HALF-LIFE BINDING PROTEINS

(75) Inventor: Robert V. Talanian, Harvard, MA (US)

(73) Assignee: Abbvie Inc., North Chicago, IL (US)

( * ) Notice: Subject to any disclaimer, the term of this patent is extended or adjusted under 35 U.S.C. 154(b) by 250 days.

(21) Appl. No.: 12/386,332

(22) Filed: Apr. 16, 2009

(65) Prior Publication Data

US 2009/0263833 A1    Oct. 22, 2009

Related U.S. Application Data

(60) Provisional application No. 61/046,062, filed on Apr. 18, 2008.

(51) Int. Cl.
*G01N 33/48* (2006.01)
*G01N 33/50* (2006.01)

(52) U.S. Cl.
USPC .......................................... 702/19; 530/388.1

(58) Field of Classification Search
CPC ................................ G06F 19/10; G06F 19/24
USPC .......................................................... 702/19
See application file for complete search history.

(56) References Cited

U.S. PATENT DOCUMENTS

2002/0147311 A1    10/2002    Gillies et al.

OTHER PUBLICATIONS

Dice et al. FASEB J., 1: 349-357, 1987.*
Cohen et al. Acta Endocrinol,1976, 83(2):243-258 (Abstract only).*
Lewitt et al Journal of Endocrinology (1993) 136, 253-260 (Abstract only).*
Bachmair et al. Science, 1986, vol. 234 No. 4773 pp. 179-186.*
Gillies et al., "Improved circulating half-life and efficacy of an antibody-interleukin 2 immunocytokine based on reduced intracellular proteolysis", Clin. Cancer Res., 8(1): 210-216 (2002).
Goldberg, A.L., "Correlation between rates of degradation of bacterial proteins in vivo and their sensitivity to proteases", Proc. Natl. Acad. Sci. U.S.A., 69(9): 2640-2644 (1972).
Mould et al., "The pharmacokinetics and pharmacodynamics of monoclonal antibodies—mechanistic modeling applied to drug development", Curr. Opin. Drug Devel., 10(1): 84-96 (2007).

* cited by examiner

*Primary Examiner* — Michael Borin
(74) *Attorney, Agent, or Firm* — Stephen J. Gaudet; Yankwich & Associates, P.C.

(57) ABSTRACT

The present invention discloses methods used to estimate the in vivo half-life of a binding protein of interest. The disclosed methods involve (a) determining for a binding protein of interest and for each of at least two different reference binding proteins an in vitro half-life using an in vitro protease reaction assay, wherein said reference binding proteins have known different in vivo half-lives, (b) determining the correlation between the known in vivo half-lives and the in vitro proteolytic half-lives of each of the reference binding proteins, and (c) estimating from said correlation between the known in vivo half-lives and the in vitro proteolytic half-lives of the reference binding proteins the in vivo half-life of the binding protein of interest that correlates with the in vitro proteolytic half-life of the binding protein of interest.

7 Claims, 1 Drawing Sheet

IN VITRO ESTIMATION OF IN VIVO HALF-LIFE BINDING PROTEINS

CROSS REFERENCE TO RELATED APPLICATION

This application claims priority to U.S. Provisional Application Ser. No. 61/046,062 filed on Apr. 18, 2008, the contents of which are incorporated herein.

FIELD OF THE INVENTION

This invention pertains generally to binding proteins. In particular, the invention provides in vitro methods for estimating the in vivo half-lives of therapeutic binding proteins.

BACKGROUND OF THE INVENTION

The duration of a therapeutic agent in the circulation of a subject depends on a variety of factors. Typically, the persistence of any agent in the circulatory system is characterized as a quantifiable pharmacokinetic value, such as the half-life ($t_{1/2}$). Depending on the particular agent, some of the more obvious factors that may affect its half-life include, but are not limited to, the sensitivity of the agent to various plasma or liver degradative activities (e.g., proteolytic, glycolytic), the solubility of the agent in the blood, the immunogenicity of the agent, the ability of the liver to filter out the agent, and the ability of it to bind to one or more serum binding proteins (e.g., serum albumin).

For many candidate therapeutic agents, the pharmacokinetic half-life is of critical importance in determining whether such candidate molecules can be developed into efficacious therapeutic agents. Thus, no matter how active a candidate molecule may appear to be toward a desired target in a high-throughput screening program such a molecule may actually have little therapeutic value if it lacks an in vivo half-life that allows the molecule to persist sufficiently long in the circulation of a subject to achieve a proper steady state concentration in order to provide a desired therapeutic benefit. Accordingly, at some point in the screening process for candidate therapeutic agents, an indication of the pharmacokinetic in vivo half-life of each prospective candidate molecule must be assessed in order to eliminate from the process those molecules that have undesirable in vivo half-lives.

Typically, the first indication of whether candidate molecules may have an acceptable in vivo half-life is obtained using small mammals, such as rats or mice. However valuable such small mammal in vivo half-life studies may be, such procedures add considerable human labor, time, and expense to the screening process. Clearly, the screening process for new therapeutic agents could be made more efficient and more economical if there were available a reliable and simple in vitro means to determine whether candidate molecules have pharmacokinetic in vivo half-lives that warrant their continued inclusion in a drug development process.

SUMMARY OF THE INVENTION

The present invention provides simple, efficient, and reliable in vitro methods for estimating the in vivo half-lives of binding proteins. In one aspect, the binding proteins of the present invention comprise therapeutic binding proteins. In another aspect, the binding proteins of the instant invention comprise reference binding proteins. In a particular aspect, the present invention provides in vitro methods for estimating the in vivo pharmacokinetic half-life ($t_{1/2}$) for binding proteins that possess one or more immunoglobulin folds (Ig). The methods are readily adapted to automated and robotic high-throughput screening procedures permitting estimation of the in vivo half-lives of multiple binding proteins in an efficient and timely manner. Accordingly, the methods are particularly useful in programs for screening and developing new therapeutic binding proteins, such as various antibody constructs directed against therapeutic targets.

One embodiment of the present invention is directed toward estimating the in vivo half-life of a binding protein of interest comprising the following steps:
  (a) determining for a binding protein of interest and for each of at least two different reference binding proteins an in vitro half-life using an in vitro protease reaction assay, wherein said reference binding proteins have known different in vivo half-lives,
  (b) determining the correlation between the known in vivo half-lives and the in vitro proteolytic half-lives of each of the reference binding proteins,
  (c) estimating from said correlation between the known in vivo half-lives and the in vitro proteolytic half-lives of the reference binding proteins the in vivo half-life of the binding protein of interest that correlates with the in vitro proteolytic half-life of the binding protein of interest.

In one aspect, the in vivo half-lives of the binding proteins refers to the half-lives in a human. Other animal species, including both vertebrate and invertebrate species, also apply to the present invention. Exemplary species include, but are not limited to, mammalian, aves, pices, reptilian, and amphibians.

In one aspect, the binding proteins of interest are therapeutic agents. In a particular aspect, the binding proteins of interest possess one or more Ig folds.

The correlation between the known in vivo half-lives of each of the reference binding proteins and their respective in vitro proteolytic half-lives as determined by a proteolytic reaction assay may be plotted to produce a reference graph (standard curve), e.g., by plotting the known in vivo half-life versus the in vitro proteolytic half-life as determined for each of the reference binding proteins. Such a standard curve may also be generated computationally without making an actual plot of the data.

A variety of suitable proteases or combinations of proteases may be used in an in vitro protease assay for estimating the in vivo half-life of a binding protein (e.g., a binding protein of interest) as described herein. Examples of suitable proteases include, but are not limited to, thermolysin, elastase, pepsin, trypsin, chymotrypsin, papain, and combinations thereof.

A reference binding protein as used herein typically binds a known cognate ligand and possesses an in vivo half-life of known value, e.g., the half-life in a human. In one aspect, the reference binding protein comprises one or more Ig folds. Examples of such reference binding proteins are known therapeutic antibody molecules as well as other known therapeutic binding proteins having, e.g., one or more Ig folds.

In one embodiment, the methods provided herein for estimating the in vivo half-life of a binding protein of interest is by determining the in vitro half-life in a proteolytic reaction assay and thereafter calculating the estimated in vivo half-life according to the linear formula:

$$y = mx + b \quad \text{(eq.1)}$$

wherein "y" is the in vivo half-life (e.g., in days), "m" is the observed slope of the linear correlation between the in vivo half-life and the in vitro protease-mediated proteolytic half-life, "x" is the in vitro half-life as determined in a proteolytic reaction assay, and the constant "b" is the y-intercept, i.e., the theoretical in vivo half-life corresponding to an in vitro proteolytic half-life of zero (x=0) along the linear correlation.

One embodiment of the present invention pertains to a method for estimating the in vivo half-life of a binding protein of interest comprises determining its in vitro half-life in a proteolysis assay and thereafter estimating its in vivo half-life that corresponds to its in vitro proteolytic half-life on a graph, i.e., a standard curve, generated by plotting in vivo half-life values versus in vitro proteolytic half-life values of at least two reference binding proteins. Such a standard curve is a graphical representation of the correlation between in vivo half-life and in vitro proteolytic half-life of reference binding proteins. An example of such a linear standard curve is shown in FIG. 1.

Figure 1:
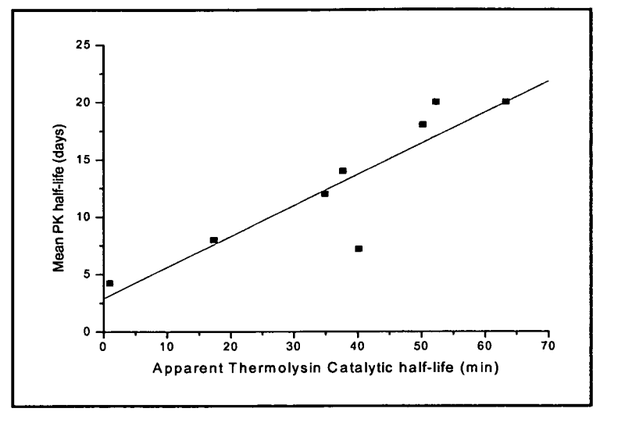
FIG. 1 is a graph (standard curve) that shows a strong linear correlation ($R^2$=0.885) between the known in vivo human half-lives and the calculated in vitro thermolysin proteolytic half-lives of reference binding proteins.

One aspect provides an alternative to using a standard curve, as illustrated in FIG. 1, is to generate a correlation or standard curve (graphically or computationally) from the known in vivo human half-lives of two or more reference binding proteins and their respective in vitro proteolytic half-lives. Advantageously, the in vitro proteolytic half-lives of reference binding proteins may be determined in parallel with or according to the identical procedure for determining the in vitro proteolytic half-life of a binding protein of interest. In this way, the in vivo half-life of the binding protein of interest is then estimated from the newly generated standard curve.

In another aspect of the invention there is provided a method for determining the relative in vivo half-lives of two or more binding proteins of interest comprising determining for each binding protein an in vitro proteolytic half-life in an in vitro proteolytic reaction assay, wherein the relative difference between the in vitro proteolytic half-lives of the binding proteins of interest indicates the relative difference between the in vivo half-lives of the binding proteins of interest. Although this method does not provide a value for each of the in vivo half-lives of the binding proteins of interest, it nevertheless permits the ordering of the binding proteins with respect to their in vivo half-lives owing to the strong correlation described for the first time herein between the in vitro proteolytic half-life and in vivo half-life of binding proteins. Such ordering is particularly useful in characterizing a population of binding proteins when the actual in vivo half-life of every member of the population is not immediately needed or required. Furthermore, the ability to order in this way a large population of binding proteins of interest according to their relative in vivo half-lives provides a means of identifying, within a population, individual binding proteins or a subpopulation of binding proteins of certain properties (e.g., longer half-life) in comparison to the rest of the population. This relative ordering or ranking of molecules enables a selection to be made for a subset of candidate molecules without immediately having to subject the entire population to in vivo testing to learn which members of the population will have the pharmacokinetic properties necessary to remain candidates for clinical development.

Thus, the methods described herein provide advantages in the discovery and development of therapeutic agents by reducing expenditure of time and resources (both in terms of expense and personnel) necessary to identify binding proteins that show promise as therapeutic agents.

DETAILED DESCRIPTION OF THE INVENTION

The present invention is based in part on the discovery that an in vitro proteolytic assay may be used to estimate an in vivo half-life for a binding protein of interest. Therapeutic binding proteins exhibit a wide range of in vivo half-lives ($t_{1/2}$). At some point in the process of screening candidate binding proteins for possible development into useful therapeutic agents, a preclinical prediction of in vivo half-life for a candidate binding protein molecule is made in order to avoid wasting further resources on a molecule that either cannot persist in the circulatory system of an animal (e.g., human) for a sufficient period of time to effectively provide the desired therapeutic benefit to a subject or that may persist for an undesirably long period of time in the circulatory system of that subject. What may be considered an acceptable in vivo half-life for a particular candidate binding protein to continue to be of interest in a drug development program will depend on the goals and judgment of the drug development practitioner, however, such an estimation must at some point be made to focus resources on one or more molecules that possess the best or optimal array of properties for being developed into efficacious therapeutic drugs. Preclinical prediction of in vivo half-life (e.g., for a human drug candidate) typically requires small mammal studies (e.g., in mice or rats) and sophisticated analytical techniques that, owing to their cost and labor, are best reserved for study of a relatively small number of candidate molecules. Therefore, the use of a simple in vitro assay that can be routinely used to predict a pharmacokinetic parameter as useful and as important as the in vivo half-life at any time in a drug screening and development process may have a tremendous impact on the overall efficiency, economics, and direction of a drug development program.

The present invention provides an in vitro assay that is unexpectedly predictive of in vivo half-life for binding proteins in a subject with surprising precision. It is based on the observation of a close correlation between the in vitro half-life in a protease cleavage assay and the in vivo half-life of known binding proteins (reference binding proteins) that are approved for administration to a subject(s) and presently available in the market. In one aspect, the subject is an animal that is either a vertebrate or invertebrate. Such vertebrates can include mammals, pices, aves, amphibians, and reptiles. In one particular aspect, the subject is a human.

In order to more clearly describe the invention the following terms are defined:

The term "binding protein" refers to any protein molecule that binds a ligand (cognate ligand, cognate binding partner). As used herein, there are two broad categories of binding proteins: (1) reference binding proteins and (2) binding proteins of interest; both are discussed below. In one aspect, the binding protein has at least one Ig fold. When the binding protein is an antibody, the ligand is an antigen. Ig folds are three-dimensional globular structural domains first identified in the variable (V) and constant (C) regions of full-length immunoglobulin molecules, i.e., full-length antibody molecules (see, e.g., Janeway and Travers, *The Immune System In Health and Disease* (Current Biology Ltd and Garland Publishing, Inc., New York, 1994), pages 3.6-3.7). An Ig fold comprises two antiparallel layers or sheets of strands of polypeptide chain, wherein each strand of polypeptide has a conformation known as a β strand, and each layer of strands is termed a β sheet. A disulfide bond links the central β strands of each β sheet such that the two β sheets are held together and form a roughly cylindrical shape (also referred to as a "Greek key barrel"). The Ig fold of a C region of an immunoglobulin molecule has two antiparallel β sheets, wherein one of the β sheets has four antiparallel β strands and the other β sheet has three antiparallel β strands. The Ig fold of a V region of an immunoglobulin molecule has two antiparallel β sheets, wherein one of the β sheets has four antiparallel β strands and the other β sheet has five antiparallel β strands.

Binding proteins that may be used in the methods described herein include full-length antibody molecules comprised of four polypeptide chains, two heavy (H) chains and two light (L) chains as well as any of a variety of antibody constructs that possess an antigen (ligand) binding domain and at least one Ig fold. As noted above, a full-length antibody molecule has multiple V and C domains and, therefore, multiple Ig folds. Antibody constructs include functional antibody fragments, fusions, mutants, variants, or derivatives of full-length antibody molecules, and such antibody constructs may have only one Ig fold. In a full-length immunoglobulin molecule (e.g., IgG, IgM, and IgA), each heavy chain is comprised of a heavy chain variable region (VH) and a heavy chain constant (CH) region. The heavy chain constant region is comprised of three domains, CH1, CH2 and CH3. Each light chain is comprised of a light chain variable region (VL) and a light chain constant region. The light chain constant region is comprised of one domain (CL). The VH and VL regions can be further subdivided into regions of hypervariability termed "complementarity determining regions" (CDR), interspersed with regions that are more conserved, referred to as "framework regions" (FR). Each VH and VL is composed of three CDRs and four FRs, arranged from amino terminus to carboxy terminus in the following order: FR1, CDR1, FR2, CDR2, FR3, CDR3, FR4. Full-length immunoglobulin molecules may be of any type (e.g., IgG, IgE, IgM, IgD, IgA, and IgY), class (e.g., IgG1, IgG2, IgG 3, IgG4, IgA1, and IgA2), or subclass.

Various antibody constructs have shown that antigen-binding function can be performed by fragments or portions of a full-length immunoglobulin molecule. Such antibody constructs may have bispecific (binding two identical antigen molecules), dual specific (binding two different antigen molecules), or multi-specific formats that can bind a combination of two or more different antigens. Examples of antibody constructs encompassed within the term "binding protein" include a Fab fragment, which is a monovalent (comprising a single binding site) fragment comprising the VL, VH, CL, and CH1 domains; a F(ab')$_2$ fragment, a bivalent (comprising two binding sites) fragment comprising two Fab fragments linked by a disulfide bridge at the hinge region; an Fd fragment comprising the VH and CH1 domains; an Fv fragment comprising the VL and VH domains of a single arm of an antibody; a single domain antibody (dAb) (Ward et al., *Nature*, 341: 544-546 (1989); Winter et al., PCT publication WO 90/05144 A1, incorporated herein by reference), which comprises a single variable domain; dual variable domain (DVD) antibodies; and isolated complementarity determining regions (CDRs) of V regions of an antibody molecule. It is well known that Fab fragments are readily generated by cleavage of a full-length antibody molecule with papain and that F(ab')$_2$ fragments can be generated by cleavage of a full-length antibody molecule with pepsin.

Although the two domains of an Fv fragment, VL and VH, are coded for by separate genes, the genes encoding the domains can be joined with a synthetic linker sequence using recombinant DNA methods so that the recombinant gene encodes a single protein chain in which the VL and VH regions are joined via a peptide linker to form a monovalent molecule known as single chain Fv (scFv) (see e.g., Bird et al. *Science*, 242: 423-426 (1988); Huston et al., *Proc. Natl. Acad. Sci. USA*, 85: 5879-5883 (1988)). Such scFv antibody constructs possess a ligand (antigen) binding domain and at least one Ig fold and therefore are encompassed by the term "binding protein" and may be used in methods described herein. Diabodies are also encompassed by the term "binding protein". Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., *Proc. Natl. Acad. Sci. USA*, 90: 6444-6448 (1993); Poljak et al., *Structure*, 2: 1121-1123 (1994)). The term "binding protein" also encompasses dual variable domain (DVD) antibodies as described, e.g., in PCT publication No. WO 2007/024715. All of the above molecules are binding proteins useful in methods described herein because they comprise a functional binding domain for a cognate binding partner, i.e., an antigen, and comprise at least one Ig fold from an immunoglobulin V or C region.

A binding protein useful in methods described herein may be a fusion protein comprising a cell receptor molecule or ligand-binding portion thereof linked to an Ig Fc region. Such fusion proteins typically possess a structure that mimics an antibody Ig molecule and, owing to the Fc region, may form dimeric or other multimeric forms in a manner similar to IgG or IgM molecules. An example of such cell receptor/Fc fusion proteins is the therapeutic drug etanercept. Etanercept is a dimeric fusion protein comprising the extracellular ligand-binding portion of the human 75 kilodalton (p75) tumor necrosis factor receptor (TNFR) linked to the Fc portion of human IgG1. The Fc component of etanercept comprises the CH2 domain, the CH3 domain, and the hinge region, but not the CH1 domain, of IgG1.

A "binding protein of interest" is any binding protein for which the in vivo (e.g., human) half-life is to be estimated using an in vitro method described herein. Depending upon the context, a binding protein of interest can be considered a therapeutic candidate.

A "reference binding protein" is a binding protein that has a known in vivo (e.g., human) half-life. Typically, the in vitro methods described herein for estimating the in vivo half-life (e.g., in human) of a binding protein of interest employs at least two reference binding proteins. Reference binding proteins useful in the methods described herein typically have different known in vivo half-lives (e.g., in human) from one another and typically also have different in vitro proteolytic half-lives in the in vitro proteolytic assay. Such differences are required to produce the correlation or standard curve between the in vivo half-life and in vitro proteolytic half-life. Use of two reference binding proteins that have different in vivo and in vitro half-lives thus provides the minimum of data needed for determining a correlation or producing a standard curve of in vivo half-life versus in vitro proteolytic half-life. Accordingly, it is within the scope of this invention to use more than two reference binding proteins in methods described herein in order to provide more data for determining the correlation between in vivo half-life and in vitro proteolytic half-life of binding proteins.

Reference binding proteins can include, but are not limited to, those therapeutic binding proteins approved for treating humans. A variety of therapeutic binding proteins have been approved for use in clinical trials or are in development for clinical use and include, e.g., rituximab (Rituxan®, IDEC/Genentech/Roche) (see, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/U.S.2003/040426, entitled "Immunoglobulin Variants and Uses Thereof"); trastuzumab (Herceptin®, Genentech) (see, U.S. Pat. No. 5,677,171), a humanized anti-Her2/neu antibody approved to treat breast cancer; pertuzumab (rhuMab-2C4, Omnitarg®), currently being developed by Genentech, an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax- EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, *Arch. Biochem. Biophys.*, 252(2): 549-60; Rodeck et al., 1987, *J Cell Biochem.*, 35(4): 315-20; Kettleborough et al., 1991, *Protein Eng.* 4(7): 773-83); ICR62 (Institute of Cancer Research) (PCT WO 95/20045; Modjtahedi et al., 1993, *J. Cell Biophys.*, 1993, 22(1-3): 129-46; Modjtahedi et al., 1993, *Br J Cancer*, 1993, 67(2):247-53; Modjtahedi et al, 1996, *Br. J. Cancer*, 73(2): 228-35; Modjtahedi et al, 2003, *Int. J. Cancer*, 105(2): 273-80); TheraCIM hR3 (YM Biosciences, Canada and Centro de Immunologia Molecular, Cuba (U.S. Pat. No. 5,891,996; U.S. Pat. No. 6,506, 883; Mateo et al, 1997, *Immunotechnology*, 3(1): 71-81); mAb-806 (Ludwig Institue for Cancer Research, Memorial Sloan-Kettering) (Jungbluth et al. 2003, *Proc. Natl. Acad. Sci. USA*, 100(2): 639-44); KSB-102 (KS Biomedix); MR1-1 (IVAX, National Cancer Institute) (PCT WO 0162931A2); and SC100 (Scancell) (PCT WO 01/88138); alemtuzumab (Campath®, Millenium), a humanized monoclonal antibody currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFα antibody developed by Centocor, adalimumab (Humira®), D2E7, an anti-TNFα antibody developed by Abbott, Humicade®, an anti-TNFα antibody developed by Celltech, golimumab (CNTO-148), a fully human TNF antibody developed by Centocor, etanercept (Enbrel®), a p75 TNF receptor Fc fusion developed by Immunex/Amgen; lenercept, a p55 TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β2 antibody being developed by Cambridge Antibody Technology, ABT 874 (J695), an anti-IL-12 p40 antibody being developed by Abbott, CAT-192, an anti-TGFPβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-γ interferon antibody being developed by Protein Design Labs, anti-α 5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-β2 integrin antibody being developed by Xoma. All of the above-cited references in this paragraph are expressly incorporated herein by reference.

Particular examples of therapeutic binding proteins useful in methods described herein include infliximab (anti-TNF-α, in vivo human half-life of 8 days), trastuzumab (anti-HER2, in vivo human half-life of 12 days), rituximab (anti-CD20, in vivo human half-life of 20 days in rheumatoid arthritis patients), palivizumab (anti-respiratory syncytial virus (RSV), in vivo human half-life of 18 days), daclizumab (anti-CD25, i.e., anti-IL-2 receptor, in vivo human half-life of 20 days), and basiliximab (anti-CD25, i.e., anti-IL-2 receptor, in vivo human half-life of 7.2 days), and etanercept (binds TNFα, in vivo human half-life of 4.25 days). The recombinant binding protein etanercept has the ligand binding portion of the p75 TNF receptor fused to an immunoglobulin Fc region, which comprises an Ig fold. Accordingly, as demonstrated in Example 2, etanercept is useful as a reference binding protein for methods described herein.

In any composition or method disclosed herein, known or disclosed equivalents of any named essential element or step may be substituted for that element or step.

Unless specifically indicated, a composition or method is not limited by any particular order of the listed elements or steps.

Unless indicated otherwise, the meaning of other terms will be clear from the context or will be understood to be the same as understood and used by persons skilled in the art.

The invention is based in part on the discovery that the calculated half-life ($t_{1/2}$) of a binding protein in an in vitro protease cleavage reaction is highly correlated with its in vivo half-life, e.g., its half-life in humans. Accordingly, methods are provided that can be used to estimate the in vivo half-life of a binding protein of interest without employing the labor, time, and expense of performing actual in vivo small mammal or human pharmacokinetic studies. In particular, methods described herein for estimating the in vivo half-life of a binding protein of interest involve calculating the in vitro proteolytic half-life for the binding protein of interest and for each of at least two reference binding proteins for which the in vivo half-lives are known. A correlation between the known in vivo half-lives and the calculated in vitro proteolytic half-lives of each of the reference binding proteins is determined (e.g., graphically or computationally). The in vitro proteolytic half-life of the binding protein of interest can then be applied to the correlation to estimate its corresponding in vivo half-life.

In one embodiment of the present invention, a method for estimating the in vivo half-life of a binding protein of interest comprises:
  (a) determining an in vitro proteolytic half-life in an in vitro protease reaction assay for each of at least two reference binding proteins and for a binding protein of interest, wherein said reference binding proteins have different known in vivo half-lives in a subject,
  (b) determining a correlation between the known in vivo subject half-lives and the in vitro proteolytic half-lives of the reference binding proteins,
  (c) estimating from the correlation between the known in vivo subject half-lives and the in vitro proteolytic half-lives of the reference binding proteins the in vivo subject half-life of the binding protein of interest that correlates with the in vitro proteolytic half-life of the binding protein of interest.

In one aspect, the subject can be an animal. Animal can include both invertebrate and vertebrates including mammals, pices, aves, reptiles, and amphibians. Mammals can include rats, mice, guinea pig, rabbit, monkey, sheep, goat, horse, and the like. In a particular aspect, subject is human.

A variety of proteases are known and readily available in the art for use in methods described herein. Such proteases include, but are not limited to, thermolysin, elastase, pepsin, trypsin, chymotrypsin, papain, and combinations thereof. Other commercially available proteases are included within the scope of this invention and are well known by those skilled in the art. A protease or combination of proteases useful in the methods described herein is one for which conditions can be optimized to provide significant, but measurable, cleavage of each of the two or more reference binding proteins as well as significantly different rates of cleavage for each of the two or more reference binding proteins. In one aspect, the in vitro proteolytic assay is performed on the proteolytic treated reference binding proteins and one or more binding proteins of interest in a day or less, in three hours or less, in two hours or less, or in one hour or less.

Any of a variety of methods known in the art may be used, alone or in combination, to follow and measure proteolytic cleavage of a protein. Such methods include, but are not limited to, polyacrylamide gel electrophoresis, electrophoresis on a microfluidic chip (see Example 2), chromatographic separation and analysis of protein or fragments thereof, immunodetection techniques to identify a protein or fragments thereof, and mass spectrometry of a binding protein or fragments thereof. Thus, a protease or combination of proteases for use in methods described herein will cleave reference binding proteins and binding proteins of interest over a period of time that permits accurate determination of the rate of cleavage and, in turn, an accurate calculation of the in vitro proteolytic half-life for each binding protein.

In one aspect, a protease or combination of proteases useful in methods described herein will cleave reference binding proteins and binding proteins of interest over a period of time that is sufficiently rapid to permit routine use in a high throughput screening program, e.g., so that in vitro proteolytic half-lives of one or more binding proteins of interest may be determined in a reasonable period of time, e.g., a day or less.

An example of a suitable protease for use in the methods described herein is thermolysin, which as shown herein (Example 2), can be used in a routine in vitro assay to cleave binding proteins in such a manner that the calculated in vitro thermolysin-mediated proteolytic half-lives are highly correlated with their respective in vivo subject half-lives, e.g., human. Thermolysin is suitable in part because conditions for proteolysis can be optimized to provide a linear correlation between the in vitro proteolytic half-life of reference binding proteins and their respective known in vivo subject half-lives.

The correlation between in vivo subject half-life and proteolytic in vitro half-life may be determined graphically by plotting the known in vivo subject half-lives of two or more reference binding proteins versus their calculated in vitro protease half-lives and drawing a best-fit standard curve (line or other shape) through the data points to reveal the correlation of in vivo subject half-life with in vitro proteolytic half-life. It is of course not necessary to actually draw such a standard curve, as any correlation can also be determined computationally, e.g., using a calculator, computer program, and the like, and simply using the computationally determined correlation to estimate the in vivo half-life of a binding protein of interest.

A suitable standard curve useful in methods described herein is a graphical representation of a linear correlation between in vivo half-life in a subject and in vitro proteolytic half-life of binding proteins. An example of such a historical standard curve is shown in FIG. 1. The accuracy of the estimation of the in vivo half-life in a subject for a binding protein of interest using a previously generated standard curve will be improved to the extent that the proteolytic reaction assay used to calculate the in vitro proteolytic half-life data of the reference binding proteins is repeated to determine the in vitro proteolytic half-life data for the binding protein of interest. For example, the linear standard curve in FIG. 1 was produced as described in Example 2; and the in vivo human half-life estimated by comparison of the in vitro proteolytic half-life of a binding protein of interest against the standard curve in FIG. 1 is most accurate as long as the in vitro proteolysis assay is performed under identical conditions to those used to generate that standard curve.

The correlation between in vivo human half-life and in vitro thermolysin proteolytic half-life shown in the standard curve in FIG. 1 is statistically significant and predictive of in vivo half-life as indicated by the square of the correlation coefficieint ($R^2$) =0.885. The closer the value of $R^2$ is to 1.00, the more predictive the in vitro half-life value is to the in vivo half-life value. An $R^2$ value of 0.885 indicates that 88.5% of the value of the data points is explained by the linear regression. Thus, an $R^2$ of 0.885 for a linear standard curve as shown in FIG. 1 objectively indicates that in vitro thermolysin-mediated cleavage of binding proteins is a valid method for predicting the in vivo human half-lives of binding proteins. Accordingly, the methods described herein that employ an in vitro thermolysin-mediated proteolytic cleavage reaction (or its equivalent) and reference binding proteins with known in vivo human half-lives provide statistically significant values for the in vivo human half-lives of binding proteins of interest. However, other proteases may be used as well in the methods described herein.

A method according to the invention for estimating the in vivo half-life of a binding protein of interest by computation, i.e., without producing a new standard curve, comprises determining the in vitro half-life in a proteolytic reaction assay using, e.g., thermolysin and thereafter calculating the estimated in vivo half-life according to the linear formula:

$$y=0.27x+2.79$$

wherein "y" is the in vivo human half-life in days, "0.27" is the slope of the linear correlation between in vivo half-life and in vitro thermolysin proteolytic half-life, "x" is the in vitro half-life in a thermolysin proteolysis assay, and the constant "2.79" is the in vivo half-life corresponding to an in vitro proteolytic half-life of zero along the linear correlation. The values for "m" and "b" in the above linear correlation formula were obtained from the standard curve of FIG. 1 that was generated from the data in Example 2 which determined the in vitro thermolysin proteolytic half-lives of the following reference binding proteins: infliximab (anti-TNF-α, in vivo human half-life of 8 days), trastuzumab (anti-HER2, in vivo human half-life of 12 days), rituximab (anti-CD20, in vivo human half-life of 20 days), palivizumab (anti-respiratory syncytial virus (RSV), in vivo human half-life of 18 days), daclizumab (anti-CD25, i.e., anti-IL-2 receptor, in vivo human half-life of 20 days), basiliximab (anti-CD25, i.e., anti-IL-2 receptor, in vivo human half-life of 7.2 days), and etanercept (binds TNF-α, in vivo human half-life of 4.25 days). Accordingly, to use the above linear correlation formula, it is necessary to determine the in vitro thermolysin proteolytic half-life of a binding protein of interest using the same reaction conditions for an assay as described in Example 2.

In an alternative procedure, it is also understood that if stocks of reference binding proteins are available, then a new correlation, i.e., a new standard curve, can be generated (graphically or computationally) for the known in vivo subject half-lives of the reference binding proteins and their respective in vitro proteolytic half-lives (such as thermolysin-mediated) as determined in parallel and at the same time as the in vitro proteolytic half-life for a binding protein of interest. In this way, an in vivo subject half-life of a binding protein of interest can be estimated from a newly generated standard curve or corresponding computational formula.

Typically, protease reaction mixtures are relatively simple to set up, run, and terminate either manually or robotically. Standard proteolytic cleavage reactions typically comprise a selected protease or combination of proteases, a buffer to provide appropriate reaction pH, any ionic species that may be required for the proteolytic activity, and a selected protein substrate (e.g., a binding protein as described herein).

Various buffers for maintaining the appropriate pH and/or other conditions for a cleavage reaction mediated by a selected protease or combination of proteases are known and readily available to the skilled practitioner in the art or are readily determined by routine optimization. In the case of a thermolysin-mediated proteolytic cleavage reaction, useful buffers include, but are not limited to, sodium acetate/calcium chloride buffer (pH around 7.8), 1× PBS/calcium chloride (pH around 7.5), and HEPES/calcium chloride.

In the case of thermolysin, a suitable thermolysin proteolytic assay useful in methods described herein comprises: binding protein (up to around 50 μg); 1× PBS/calcium chloride (pH of about 7.5); and thermolysin (e.g., about 2 to about 4 units for thermolysin as available from Sigma-Aldrich Co. (St. Louis, Mo., catalog No. T7902). In one aspect, the reaction is run at approximately 37° C. and samples are periodically removed to analyze cleavage of binding protein.

A proteolytic cleavage reaction may be terminated by any of a variety of means. If a divalent metal ion is critical to protease activity (e.g., calcium, magnesium), then the proteolytic cleavage reaction may be easily terminated by addition of one or more metal ion chelators, such as EDTA or EGTA. Alternatively, a proteolytic cleavage reaction may be terminated by more general means including, but not limited to, denaturation of the protease by heating or boiling, denaturation by chemical reagent (e.g., detergent, organic solvent, chaotropic agent), and selective removal of protease or substrate from the reaction mixture (e.g., when the protease or its substrate is linked to a retrievable particle or other solid substrate that can be sequestered or otherwise separated from the reaction mixture).

As noted above, the determination of the amount of cleavage of binding protein or, alternatively, the remaining fraction of uncleaved binding protein over time in an in vitro proteolytic cleavage reaction is easily obtained by methods available in the art (e.g., electrophoretic methods, immunodetection methods, mass spectrometry). For example, samples that are removed at various times from an in vitro proteolytic cleavage reaction of a binding protein can be electrophoresed through a polyacrylamide gel, and the gel stained or subjected to immunoblotting to reveal one or more bands corresponding to binding protein molecules and/or cleavage fragments thereof. In this way, it is possible to monitor the disappearance of a gel band corresponding to uncleaved binding protein over the course of the proteolytic cleavage reaction. The remaining fraction of uncleaved binding protein can then be quantified at each time point, e.g., by scanning the particular gel band at each time point (i.e., lane in the gel) with a laser densitometer, or equivalent instrument. A recent improvement in standard electrophoretic analysis of proteolytic cleavage products is to use a microfluidic chip coupled with appropriate computer software. An example of using a microfluidic chip is provided in Example 2. Such microfluidic chips employ very small sample volumes (e.g., microliters, nanoliters) for separating and analyzing proteins in a sample. Separated proteins in an electrophoretic migration may be detected and quantified using laser-induced fluorescence, and the data compiled and analyzed by appropriate software in a computer linked to the chip. The data can be processed to produce a virtual gel image to illustrate the electrophoretic separation and migration of proteins in the sample.

The disappearance of a protein band corresponding to uncleaved binding protein (in a gel band or on a virtual gel band) can thus be monitored and quantified over the course of a proteolytic cleavage reaction by various methods. The amount of a protein band can be plotted graphically or computationally against reaction time to determine the in vitro proteolytic half-life. The apparent pseudo-first order rate constant of decay ($K_{app}$) and the apparent half-life ($t_{1/2}$) for a binding protein in an in vitro proteolytic cleavage reaction are readily calculated by standard formulae familiar to those skilled in the art. The remaining uncleaved fraction (r) of a binding protein can then be quantified by measuring the area under the curve of the remaining protein (y) at a specific time (t) divided by the area under the curve of the uncleaved antibody ($y_0$) at time zero ($r=y/y_0$). Plotting the remaining fraction (r) versus time provides the exponential decay function that describes the cleavage of the binding protein mediated by the protease. Thus, in the case of a linear correlation, the standard formula $r=e^{-(Kapp \times t)}$ can then be solved to obtain the apparent pseudo-first order rate constant $K_{app}$, which in turn can be used to calculate the in vitro proteolytic half-life of the binding protein from the standard formula $t_{1/2}=\ln 2/K_{app}$.

The in vitro proteolytic half-lives of two or more reference binding proteins can then be plotted (graphically or computationally) against their respective known in vivo human half-lives. As noted above, a historical reference line (standard curve) in FIG. 1 can be used to estimate the in vivo human half-life of a binding protein of interest for which an in vitro proteolytic half-life has been obtained in a thermolysin-mediated proteolysis reaction using the reactions conditions described in Example 2. The accuracy of the in vivo half-life estimated using FIG. 1 is improved to the extent that the thermolysin proteolytic reaction assay used to produce the in vitro proteolytic half-life data of the reference binding proteins is repeated to produce the in vitro proteolytic half-life data for a binding protein of interest.

Owing to the discovery that an in vitro proteolytic half-life of a binding protein is strongly correlated with the in vivo human half-life of the binding protein, in vitro proteolytic half-lives may be used to obtain two or more binding proteins of interest with respect to their in vivo half-lives on a relative basis, i.e., in the absence of making an estimation of the in vivo half-lives as described above. Such an ordering of binding proteins of interest has particular value in high throughput screening of relatively large numbers of candidate binding proteins for use in therapy. For example, a relatively wide range of differences between in vitro proteolytic half-lives among various binding proteins of interest indicates a wide range of differences in their respective in vivo half-lives. In such a case, the practitioner may decide that it is more efficient and economical to focus further screening or development on a subgroup containing binding proteins that have relatively high in vitro proteolytic half-lives in comparison to other binding proteins.

In studies or procedures to modify or improve one or more properties of a binding protein of interest, the in vitro proteolytic half-life is an easily obtained indication of whether a modification will impact the in vivo half-life of the binding protein of interest, either adversely or in a desirable manner. For example, in a program of affinity maturation, wherein a family of antibody molecules is created having small variations, e.g., in one or more of the CDRs of a parental antibody molecule, all members of the family may have acceptable binding affinity for a particular antigen, but the impact of the variations may have a detrimental impact on other desirable properties, such as in vivo half-life. In such a situation, methods described herein are useful to determine which members of a family of antibody molecules have relatively longer in vivo half-lives and which have relatively short in vivo half-lives.

It is understood that the conditions for an in vitro proteolytic assay used in methods described herein are designed to obtain in vitro proteolytic half-lives for the two or more reference binding proteins and, in turn, to generate a correlation or standard curve for predicting the in vivo half-life of a binding protein of interest. As with any assay involving a correlation or standard curve, the most reliable values for the in vivo half-life of binding proteins of interest will be those that are obtained within the region of the correlation or standard curve that is between data points of two or more reference binding proteins, i.e., where values are interpolated between reference data, and less reliable values for in vivo half-lives of binding proteins of interests are likely to be those that are obtained outside that region of the correlation or standard curve, i.e., where values are extrapolated beyond the data of reference binding proteins.

Additional embodiments and features of the invention will be apparent from the following non-limiting examples.

EXAMPLES

Example 1

Initial Screening of Proteases for in vitro Partial Cleavage Reactions of Therapeutic Reference Binding Proteins Trypsin, elastase, chymotrypsin, and thermolysin were initially tested for the ability to provide differing rates of cleavage of binding proteins with known in vivo human half-lives. Standard protease cleavage reaction conditions were employed, and the course of cleavage of each binding protein by each of the proteases was followed over time using polyacrylamide gel electrophoresis.

Stock preparations (10 mg/mL) were prepared in 1× phosphate buffered saline (PBS) of the following binding proteins (i.e., reference binding proteins): infliximab (REMICADE® infliximab, Centocor, Inc., Horsham, Pa.), trastuzumab (HERCEPTIN® trastuzumab, Genentech, Inc., South San Francisco, Calif.), rituximab (RITUXAN® rituximab, Genentech, Inc., South San Francisco, Calif. and Biogen IDEC, Cambridge, Mass.), palivizumab (SYNAGIS® palivizumab, MedImmune, Inc., Gaithersburg, Md.), daclizumab (ZENAPAX® daclizumab, Hoffmann-La Roche Inc., Nutley, N.J.), basiliximab (SIMULECT® basiliximab, Novartis International AG, Basel, Switzerland), and etanercept (ENBREL® etanercept, AMGEN, Thousand Oaks, Calif. and Wyeth Pharmaceuticals, Inc., Philadelphia, Pa.).

This initial analysis indicated that all of the binding proteins were susceptible to some degree of cleavage by each of the proteases. For example, thermolysin was effective in providing observable cleavage of each reference binding protein over time as well as in providing different rates of proteolytic cleavage for each reference binding protein. Data from the thermolysin-mediated proteolysis of each of the above-mentioned reference binding proteins are shown in Table 1.

TABLE 1

Thermolysin-Mediated Cleavage of Reference Antibody Molecules

| Reference Binding Protein | Percent Remaining Fraction of Reference Binding Proteins at Indicated Reaction Times (minutes) Reaction Time (min) | | | | | | | | | |
|---|---|---|---|---|---|---|---|---|---|---|
| | 0 | 10 | 20 | 30 | 45 | 60 | 80 | 100 | 120 | 150 |
| infliximab | 100 | 62.07 | 84.44 | 49.79 | 28.3 | 16.65 | 11.96 | 6.95 | 12.56 | 7.35 |
| trastuzumab | 100 | 130.78 | 107.75 | 114.99 | 91.16 | 65.05 | 46.35 | 28.54 | 29.27 | 26.86 |
| rituximab | 100 | 87.75 | 88.88 | 103.2 | 79.69 | 65.7 | 50.52 | 36.56 | 29.35 | 21.18 |
| palivizumab | 100 | 89.05 | 61.48 | 71.52 | 53.75 | 42.12 | 31.37 | 21.25 | 20.1 | 12.18 |
| daclizumab | 100 | 102.75 | 105.21 | 100.96 | 78.16 | 63.28 | 47.16 | 47.88 | 32.44 | 23.78 |
| basiliximab | 100 | 94.72 | 84.88 | 67.6 | 51.89 | 38.59 | 34.42 | 17.67 | 15.06 | 11.84 |
| etanercept | 100 | 20 | 0 | 0 | 0 | 0 | 0 | 0 | 0 | 0 |

Example 2 in vitro Thermolysin Proteolysis to Estimate in vivo Half-Life ($t_{1/2}$) of Binding Proteins of Interest This example demonstrates a highly linear correlation between in vivo human half-life ($t_{1/2}$) and in vitro thermolysin-mediated proteolytic half-life of binding proteins.

Materials and Methods

Thermolysin from Bacillus thermoproteolyicus rokko was obtained from Sigma-Aldrich Co. (St. Louis, Mo., catalog No. T7902).

10× Reaction Buffer: 500 mM sodium acetate, 100 mM calcium chloride, pH=7.

HT Protein Express LabChip microfluidic chip Kit (Lot No. B911A, Caliper Life Sciences, Hopkinton, Mass.).

96-well polymerase chain reaction (PCR) microplates (catalog no. PCR-96-FS-C, Axygen Scientific, Inc., Union City, Calif.).

Stop Solution: 0.5 M EDTA, pH 7.5.

Denaturation Buffer: HT protein sample buffer containing LDS from Caliper Life Sciences (This proprietary buffer is provided by the manufacturer of Labchip LC90).

Binding Protein Molecule Proteolysis and Analysis

Binding protein solutions (1 mg/mL) were prepared in 1× PBS. Thermolysin protease solution was resuspended in water at 8 mg/mL prior to initiating proteolytic cleavage reaction.

Thermolysin protease cleavage reaction:
  A 1.5 mL eppendorf reaction tube contained:
  40 µL of binding protein (1 mg/mL),
  5 µL 10× Reaction Buffer to make 1× Reaction Buffer,
  5 µL thermolysin (8 mg/mL) to make 1:1 (w:w) antibody:protease ratio.

The cleavage reaction was incubated at 37° C. At specified times during the cleavage reaction, samples (4 µL) were removed and mixed with EDTA Stop Solution (2 µL) in wells of a 96-well PCR microplate. Denaturation buffer (6 µL) was added to each well, and the microplate incubated at room temperature (RT) for 2 hours or overnight. Then, 10 µL of water was added to each well before reading on a LabChip Caliper 90 microfluidic chip prepared and used according to manufacturer's instructions. A reading of a control sample (no thermolysin) at time=0 is critical for quantification of proteolytic cleavage. Samples of the thermolysin proteolytic cleavage reactions were removed and terminated at 0, 10, 20, 45, 60, 80, 100, 120, and 150 minutes. A control sample (no thermolysin) was also taken at 150 minutes as a check on the stability of the antibody molecule.

Results

Commercially available preparations of reference binding proteins with known in vivo human half-lives served as substrates in an in vitro thermolysin-mediated proteolytic cleavage reaction. Thermolysin provided significant, but measurable, cleavage of each reference binding protein as well as significantly different rates of cleavage of each reference binding protein. The respective in vitro rates of cleavage (per minute) were determined for each binding protein. The in vitro proteolytic rates of cleavage were then used to calculate the corresponding apparent thermolysin-mediated proteolytic (catalytic) half-lives (minutes).

Table 2 summarizes the apparent in vitro proteolytic cleavage rate (per minute), the apparent in vitro proteolytic half-life (minutes), and the published mean in vivo human half-life (days) for each therapeutic binding protein.

TABLE 2

| Reference Binding Protein | Apparent Proteolytic Rate of Cleavage (min$^{-1}$) | Apparent Proteolytic Half-Life ($t_{1/2}$) (min) | Published Mean In Vivo Human Half-Life (days) |
|---|---|---|---|
| infliximab | 0.03995 | 17.35 | 8 |
| trastuzumab | 0.01985 | 34.92 | 12 |
| rituximab | 0.01325 | 52.31 | 20 |
| palivizumab | 0.0138 | 50.23 | 18 |
| daclizumab | 0.01095 | 63.30 | 20 |
| basiliximab | 0.01726 | 40.16 | 7.2 |
| etanercept | ND | <1 | 4.25 |

The plot of the published mean human pharmacokinetic in vivo half-life (days) versus in vitro thermolysin-mediated proteolytic half-life (minutes) provides the standard curve shown in FIG. 1. Remarkably, the square of the correlation coefficient ($R^2$) for this standard curve is 0.885 indicating a high degree of correlation between the in vitro thermolysin-mediated proteolytic half-life of a binding protein and its corresponding in vivo human half-life. This high value for $R^2$ demonstrates that the in vitro thermolysin-mediated cleavage of binding proteins is a valid model for the predominant mechanism limiting the in vivo human half-lives of binding proteins. Thus, the in vitro thermolysin proteolytic half-life for any binding protein as determined using the thermolysin cleavage reaction conditions described in this study can be used to estimate the respective in vivo human half-life from the standard curve shown in FIG. 1.

All patents, applications, and publications cited in the above text are incorporated herein by reference.

Other variations and embodiments of the invention described herein will now be apparent to those of ordinary skill in the art without departing from the scope of the invention.

What is claimed is:

1. A method for estimating the in vivo human half-life of a monoclonal antibody of interest comprising:
    (a) determining an in vitro proteolytic half-life in an in vitro protease reaction assay for each of at least four different reference monoclonal antibodies and for said antibody of interest, wherein said reference antibodies have different known in vivo human half-lives and wherein said in vitro protease reaction assays are performed under identical conditions,
    (b) determining a correlation between the known in vivo human half-lives and the in vitro proteolytic half-lives of the reference antibodies,
    (c) estimating from the correlation in (b) between the known in vivo human half-lives and the in vitro proteolytic half-lives of the reference antibodies the in vivo human half-life of the antibody of interest that correlates with the in vitro proteolytic half-life of the antibody of interest.

2. The method according to claim 1, wherein said correlation is a linear correlation.

3. The method of claim 1, wherein said protease is selected from the group consisting of thermolysin, elastase, pepsin, trypsin, chymotrypsin, papain, and combinations thereof.

4. The method according to claim 3, wherein said protease is thermolysin.

5. The method according to claim 2, wherein said correlation is linear and represented by the formula:

$$y = mx + b$$

wherein "y" is the in vivo human half-life, "m" is the observed slope of the linear correlation between the in vivo human half-life and the in vitro protease-mediated proteolytic half-life, "x" is the in vitro half-life as determined in a proteolytic reaction assay, and the constant "b" is the y-intercept corresponding to an in vitro proteolytic half-life of zero (x = 0) along the linear correlation.

6. The method according to claim 1, wherein said at least four reference antibodies are selected from the group consisting of infliximab, trastuzumab, rituximab, palivizumab, daclizumab, and basiliximab.

7. The method of claim 1, wherein said correlation is linear and represented by the formula:

$$y = 0.27x + 2.79$$

wherein "y" is the in vivo human half-life in days, "0.27" is the slope of the linear correlation between in vivo human half-life and in vitro thermolysin proteolytic half-life, "x" is in vitro half-life in an in vitro thermolysis proteolysis assay, and the constant "2.79" is the in vivo human half-life corresponding to an in vitro proteolytic half-life of zero (0 days) along the linear correlation.

* * * * *